United States Patent
Yamashita

[19]
[11] Patent Number: 5,986,456
[45] Date of Patent: Nov. 16, 1999

[54] SURFACE POTENTIAL SENSOR AND PROCESSING CIRCUIT HAVING IMPROVED NOISE REDUCTION

[75] Inventor: Muneharu Yamashita, Toyama-ken, Japan

[73] Assignee: Murata Manufacturing Co., Ltd., Japan

[21] Appl. No.: 08/927,628

[22] Filed: Sep. 11, 1997

[30] Foreign Application Priority Data

Sep. 12, 1996 [JP] Japan ................................ 8-241643

[51] Int. Cl.⁶ ............................ G01R 29/12; G01N 27/60
[52] U.S. Cl. ........................ 324/457; 324/458; 324/613; 324/452
[58] Field of Search .................... 324/452, 457, 324/458, 613, 614, 72

[56] References Cited

U.S. PATENT DOCUMENTS

| | | | |
|---|---|---|---|
| 4,267,511 | 5/1981 | Suzuki et al. | 324/458 |
| 5,065,102 | 11/1991 | Takanashi et al. | 324/452 |
| 5,270,660 | 12/1993 | Werner, Jr. et al. | 324/458 |
| 5,600,251 | 2/1997 | Akiyama | 324/458 |

FOREIGN PATENT DOCUMENTS 59-15864  1/1984  Japan ...................... 324/458

*Primary Examiner*—Diep N. Do
*Attorney, Agent, or Firm*—Ostrolenk, Faber, Gerb & Soffen, LLP

[57] ABSTRACT

A surface potential sensor which is less affected by noise superposed on a reference source voltage than prior sensors, and hence can improve measurement accuracy with ease, and which also has higher stability against extraneous noise. The sensor includes an initial-stage input circuit comprising an FET, and a succeeding-stage amplifier circuit mainly comprising an operational amplifier for amplifying a difference between an AC component from the initial-stage input circuit and a reference source voltage. A resistor is connected between a drain of the FET constituting the initial-stage input circuit and a source voltage line to take out a signal from the FET drain. The source voltage supplied to the FET is the reference source voltage.

9 Claims, 5 Drawing Sheets

SURFACE POTENTIAL SENSOR AND PROCESSING CIRCUIT HAVING IMPROVED NOISE REDUCTION

BACKGROUND OF THE INVENTION

1. Field of the Invention

The present invention relates to a surface potential sensor for being positioned to face a charged member for detecting a surface potential of the charged member.

2. Description of the Related Art

In apparatus utilizing static electricity, such as PPC copying machines, page printers and electrostatic dust collectors, surface potential sensors have been heretofore employed to detect a surface potential of a charged member and keep the surface potential stable.

The principle of measuring a surface potential of a charged member will be described with reference to FIG. 5. In FIG. 5, when a detecting electrode is placed near a charged member which is to be measured and has a surface potential Vx, an electrostatic capacitance C is produced between the detecting electrode and the charged member to be measured. By periodically changing the distance between the detecting electrode and the charged member to be measured, the electrostatic capacitance C is changed correspondingly and a resulting voltage across a resistor R is output as Vout.

FIG. 6 is a block diagram of a surface potential sensor for measuring a surface potential of a charged member to be measured in accordance with a signal output from the circuit shown in FIG. 5. The distance between the detecting electrode and the charged member to be measured is periodically changed by using a tuning fork, for example, as shown in FIG. 6. A piezoelectric tuning-fork oscillator circuit vibrates the tuning fork with a constant amplitude. An initial-stage input circuit performs impedance conversion by receiving a voltage output from the detecting electrode under high input impedance and outputting a detection signal under low output impedance. A succeeding-stage amplifier circuit amplifies an AC component of the detection signal, a rectifier circuit rectifies the AC-amplified signal, and a DC amplifier circuit amplifies the rectified signal with a constant gain before outputting it as a measured voltage. A stabilized power supply circuit supplies stabilized source voltages to the various circuits.

FIG. 7 is a circuit diagram including the initial-stage input circuit and the succeeding-stage amplifier circuit in FIG. 6. As shown in FIG. 7, the initial-stage input circuit is of the source follower type made up by connecting a drain of an FET to a source voltage Vc, a resistor R3 between a source of the FET and ground, and a resistor R2 between the detecting electrode and a gate of the FET. Additionally, a resistor R1 is connected between the detecting electrode and ground. An operational amplifier OP1 has a non-inverted input terminal to which are applied a reference source voltage Vr through a resistor R5 and the AC component of a signal from the FET source through a capacitor C1. A voltage dividing circuit comprised of resistors R6, R7 is connected to an output terminal of the operational amplifier OP1. Further, a feedback circuit comprised of the voltage dividing circuit, resistors R8, R9 and capacitors C2, C3 is associated with the operational amplifier OP1. The succeeding-stage amplifier circuit using an operational amplifier is thus constructed.

The conventional surface potential sensor including the initial-stage input circuit and the succeeding-stage amplifier circuit, shown in FIG. 7, has a problem which can occur if noise is superposed on the reference source voltage Vr. Specifically, the operational amplifier OP1 amplifies a difference between the FET output (AC component) and the reference source voltage Vr. Accordingly, if noise is superposed on the reference source voltage Vr for some reason, the operational amplifier OP1 amplifies the noise component as well, resulting in a risk that detection accuracy of the surface potential may be lowered, or that a detection characteristic may be deteriorated. In particular, because the operational amplifier OP1 of the succeeding-stage amplifier circuit shown in FIG. 7 must amplify a weak voltage signal on the order of 10 $\mu$V–100 mV, the effect caused by the noise superposed on the reference source voltage Vr becomes relatively large.

SUMMARY OF THE INVENTION

The present invention is able to provide a surface potential sensor which is less affected by noise superposed on a reference source voltage, and which can improve measurement accuracy with ease.

The present invention can further provide a surface potential sensor which has higher stability against extraneous noise.

To achieve the above advantages, according to a first aspect of the present invention, in a surface potential sensor comprising a detecting electrode positioned to face a charged member for detecting a surface potential of the charged member, an arrangement for periodically changing an electrostatic capacitance formed between the charged member and the detecting electrode, an initial-stage input circuit connected to the detecting electrode, and a succeeding-stage amplifier circuit connected downstream of the initial-stage input circuit and including an operational amplifier for amplifying a difference between an AC component from the initial-stage input circuit and a reference source voltage, a source voltage supplied to the initial-stage input circuit is derived from the reference source voltage so that the sensor is not affected by noise superposed on the reference source voltage. Even with noise superposed on the reference source voltage, therefore, no noise component appears in the difference between the AC component output from the initial-stage input circuit and the reference source voltage. The subsequent-stage amplifier circuit can therefore amplify the AC component without being affected by the noise component. Consequently, measurement accuracy can be improved with ease.

According to a second aspect of the present invention, the initial-stage input circuit in the surface potential sensor is made up by grounding a source of an FET and connecting a resistor between a drain of the FET and a power source. A signal from the detecting electrode is applied between a gate of the FET and ground, and a drain potential of the FET is applied to the subsequent-stage amplifier circuit through a capacitor.

According to a third aspect of the present invention, a line which supplies the reference source voltage and a ground electrode are arranged in a position close to the detecting electrode and also close to a gate terminal of the FET or an input circuit portion leading to the gate terminal. Since the reference source voltage is usually output from a power supply circuit having low output impedance, the reference source voltage line is effective to serve as a shield electrode. With the above arrangement, therefore, the detecting electrode and either the gate terminal of the FET or the input circuit portion leading to the gate terminal are shielded-by the reference source voltage line and the ground electrode. Consequently, the sensor is less affected by extraneous noise.

DESCRIPTION OF AN EMBODIMENT OF THE INVENTION

Figure 1A:
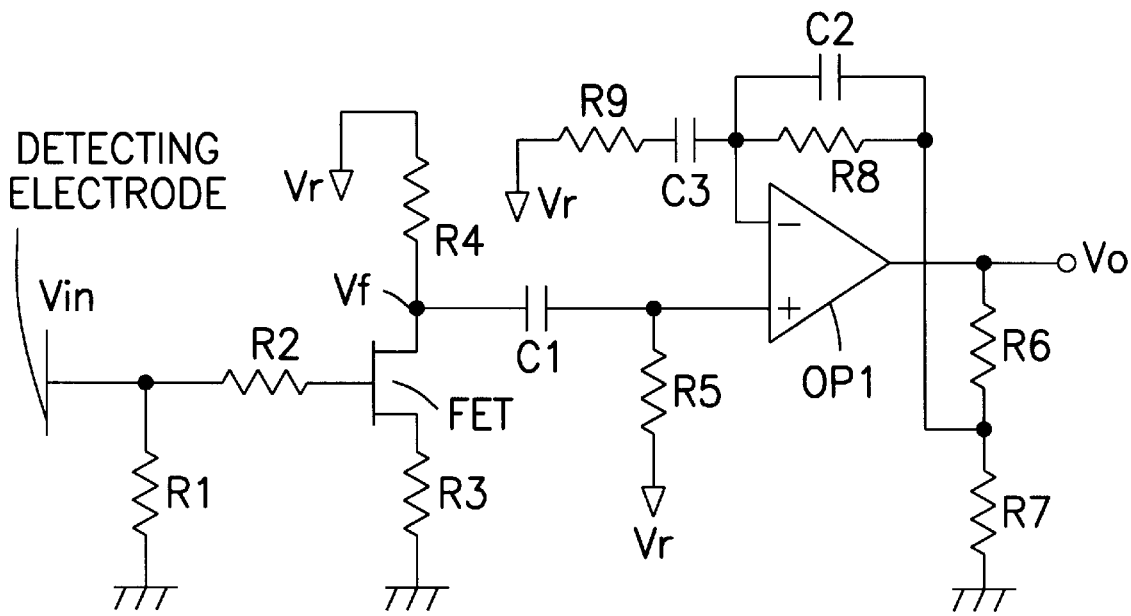
FIG. 1A is a circuit diagram of an initial-stage input circuit and a succeeding-stage amplifier circuit of a surface potential sensor according to an embodiment of the present invention.

FIG. 1A is a circuit diagram of a principal section of a surface potential sensor according to an embodiment of the present invention, showing an initial-stage input circuit and a succeeding-stage amplifier circuit. As shown, the initial-stage input circuit is made up by connecting a resistor R4 between a drain of an FET and a line from a reference source voltage Vr, grounding a source of the FET through a resistor R3, connecting a resistor R2 between a gate of the FET and a detecting electrode, and connecting a resistor R1 between the detecting electrode and ground. An operational amplifier OP1 has a non-inverted input terminal which is connected to the line from the reference source voltage Vr through a resistor R5 and is connected to the drain of the FET through a capacitor C1. A voltage dividing circuit comprised of resistors R6, R7 is connected between an output terminal of the operational amplifier OP1 and the ground. Further, a feedback circuit comprised of the voltage dividing circuit, resistors R8, R9 and capacitors C2, C3 is associated with the operational amplifier OP1. The succeeding-stage amplifier circuit is thus constructed.

Because of the feedback circuit comprised of the resistors R6, R7, R8, R9 and the capacitors C2, C3 associated with the operational amplifier OP1, the operational amplifier OP1 serves as an AC amplifier circuit having a band pass filter characteristic. Its frequency pass band and gain are determined by circuit constants of the components of the feedback circuit.

Figure 1B:
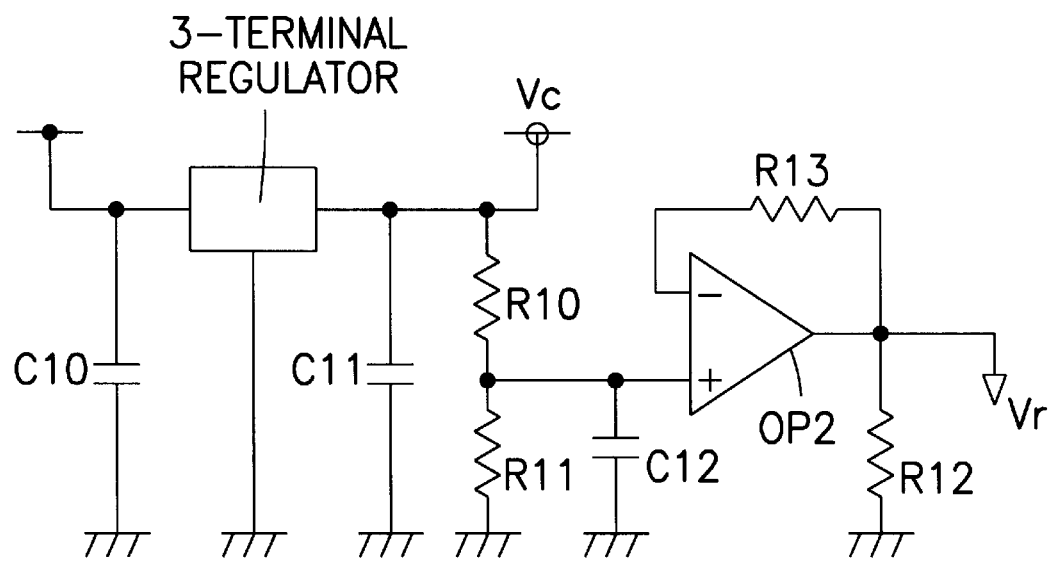
FIG. 1B is a circuit diagram of a power supply circuit of a surface potential sensor according to an embodiment of the present invention.

FIG. 1B is a diagram of a power supply circuit for generating the reference source voltage Vr. As shown, a 3-terminal regulator has an input terminal and an output terminal to which capacitors C10, C11 are connected, thereby generating a stabilized source voltage Vc. A voltage dividing circuit is made up of resistors R10, R11 and connected to the output portion of the 3-terminal regulator.

A filter circuit is made up of those resistors R10, R11 and a capacitor C12, and is connected to a non-inverted input terminal of an operational amplifier OP2. The operational amplifier OP2 has an output terminal which is connected to ground through a resistor R12 and is connected to an inverted input terminal of the amplifier OP2 through a resistor R13. A so-called voltage follower type circuit is thereby constructed to generate the reference source voltage Vr.

Assuming now that the FET has an input voltage Vin, an output voltage Vf, a drain current Id, a mutual conductance $g_{fs}$, and a gain $\alpha$, there holds the following relationship:

$$\begin{aligned} Vf &= Vr - Id\ R4 \\ &= Vr - Vin \cdot g_{fs} \cdot R4 \\ &= Vr - \alpha Vin \end{aligned}$$

Also assuming that the AC amplifier circuit mainly constituted by the operational amplifier OP1 has a gain A, its output voltage Vo is expressed by:

$$\begin{aligned} Vo &= (Vf - Vr)A \\ &= (Vr - \alpha Vin - Vr)A \\ &= - A\alpha Vin \end{aligned}$$

This means that the output voltage Vo of the AC amplifier circuit is independent of Vr and is therefore not affected by the noise component superposed on the reference source voltage Vr.

Figure 7:
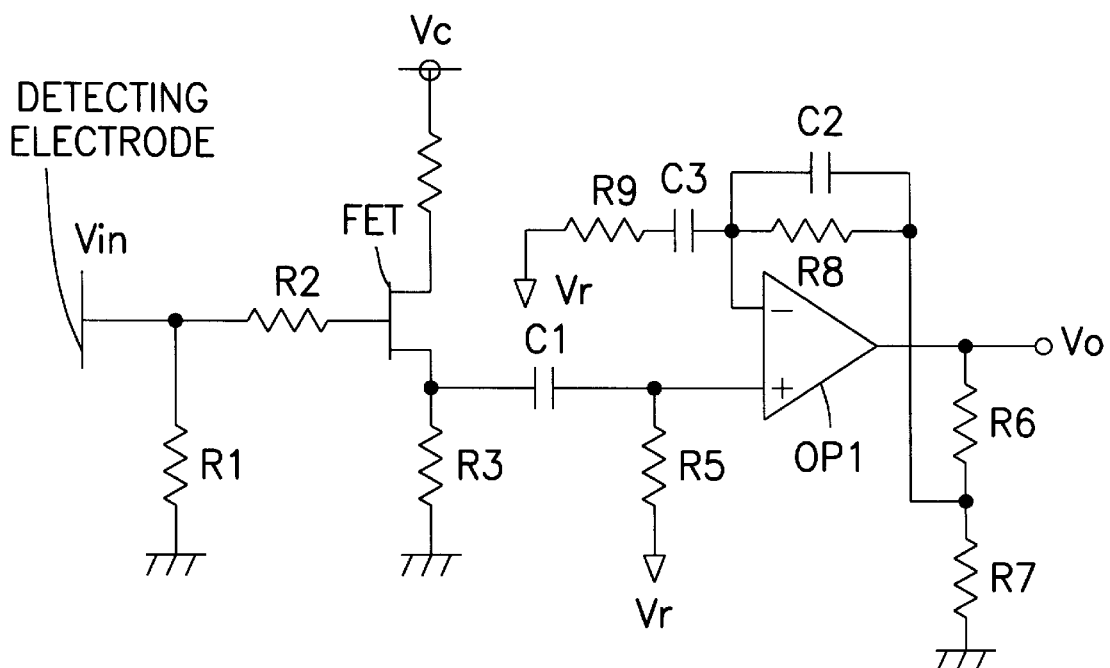
FIG. 7 is a circuit diagram of an initial-stage input circuit and a succeeding-stage amplifier circuit of the conventional surface potential sensor.

The amplifier circuit comprising the FET which is shown in FIG. 7 has an amplification factor expressed by:

$$Vf/Vin = g_{fs} \cdot R3/(1+g_{fs} \cdot R3)$$

whereas an amplification factor by which the FET shown in FIG. 1 amplifies the signal component is expressed by;

$$Vf/Vin = (-g_{fs} R4)/(1+g_{fs} \cdot R3)$$

On the assumption that R4=R3, therefore, the initial-stage input circuit shown in FIG. 1 has the same amplification factor as the conventional initial-stage input circuit shown in FIG. 7 although the phase is just inverted.

Figure 2:
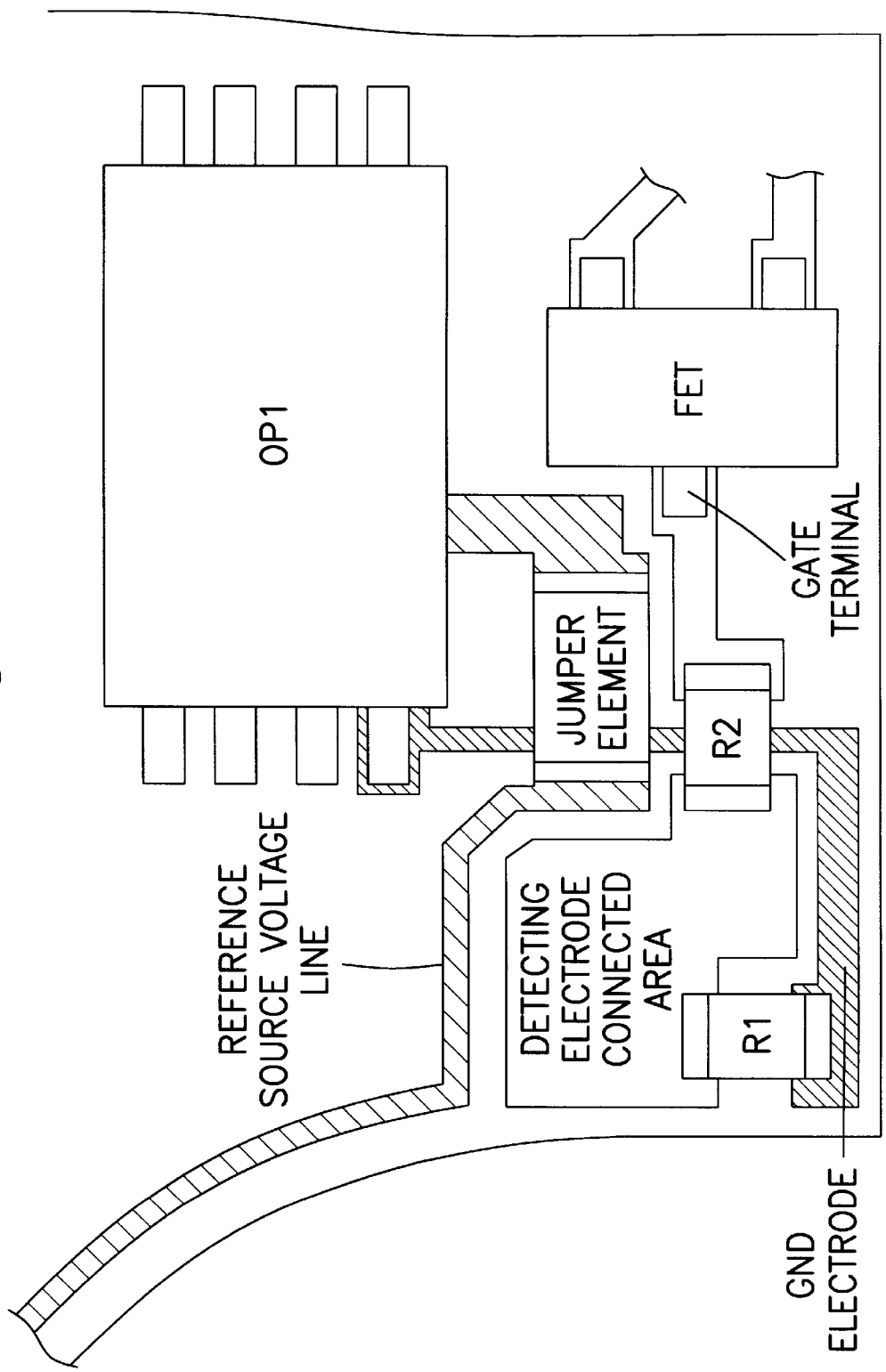
FIG. 2 is a diagram showing the layout of principal parts of the surface potential sensor on a circuit board.

FIG. 2 is a diagram showing the layout of principal parts of the surface potential sensor on a circuit board.

In FIG. 2, R1, R2, FET and OP1 correspond to the parts denoted by the same characters in FIG. 1, and the detecting electrode is connected to a detecting electrode connected area in FIG. 2. As shown, the reference source voltage line and a GND (ground) electrode are arranged in positions close to the resistors R1, R2, the detecting electrode connected area, and the gate of the FET. Specifically, the reference source voltage line and the GND electrode are extended and shaped so as to closely surround the detecting electrode connected area and the resistor R1, thereby establishing driven shield of the input portion of the initial-stage input circuit. This layout contributes to suppressing the effect of extraneous noise. When the reference source voltage line is so extended, extraneous noise is more likely to be superposed on the reference source voltage. With the present invention, however, a surface potential of a charged member to be measured can be detected without being affected by the noise superposed on the reference source voltage, as mentioned above. Accordingly, the reference source voltage line can be extended as necessary so that a sufficient degree of driven shield may be provided.

Figure 3A:
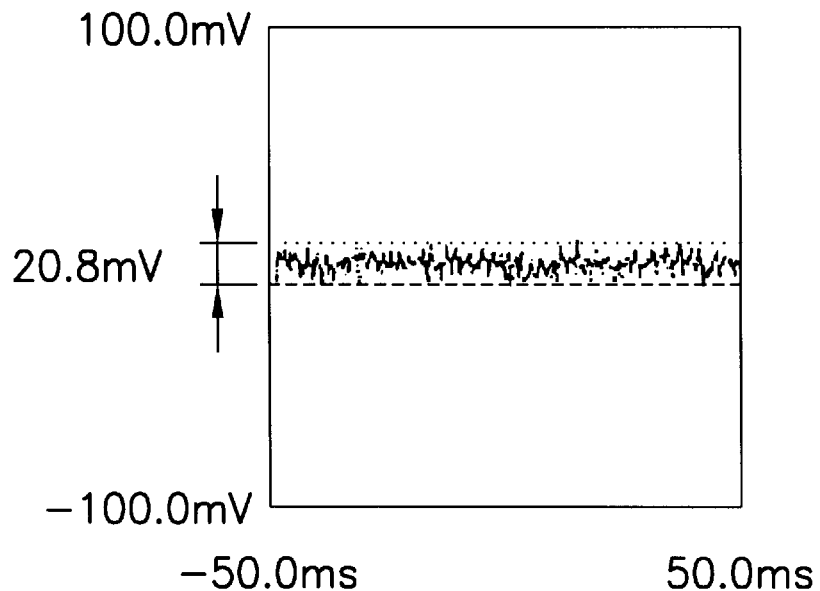
FIGS. 3A and 3B are graphs showing respectively an effect of noise superposed on a reference source voltage in an embodiment of the invention and in the conventional surface potential sensor.
Figure 3B:
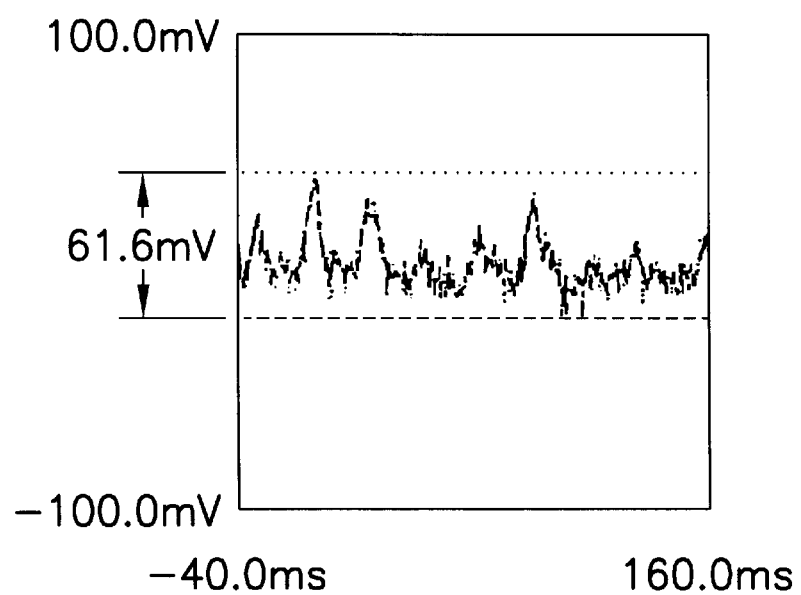

Next, graphs of FIGS. 3A and 3B show the effect of noise superposed on the reference source voltage in the embodiment of the present invention, and in the conventional surface potential sensor, respectively. FIG. 3A represents an output waveform of Vo when Vin=0 is set in FIG. 1 (i.e., when the surface potential of a charged member to be measured is made zero), and FIG. 3B represents an output waveform of Vo when Vin=0 is set in FIG. 7. In the graph of FIG. 3A, the vertical axis covers a range of −100.0 mV to 100.0 mV and the horizontal axis covers a range of −50.0 ms to 50.0 ms. In the graph of FIG. 3B, the vertical axis covers a range of −100.0 mV to 100.0 mV and the horizontal axis covers a range of −40.0 ms to 160.0 ms. The occurrence of noise despite Vin=0 is attributable to extraneous noise and characteristics of the operational amplifier OP1 and the FET. In the conventional circuit shown in FIG. 7, noise (popcorn noise) generated by the 3-terminal regulator and the operational amplifier OP2 and superposed on the reference source voltage are amplified by the operational amplifier OP1 and, as shown in FIG. 3B, appears as a large noise component (61.6 mVpp in the plotted example) in the output waveform. By contrast, in the present embodiment of the invention, because the sensor is not affected by the noise superposed on the reference source voltage, the noise component contained in the output waveform is sufficiently suppressed (down to 20.8 mVpp in the plotted example), as shown in FIG. 3A.

Figure 4:
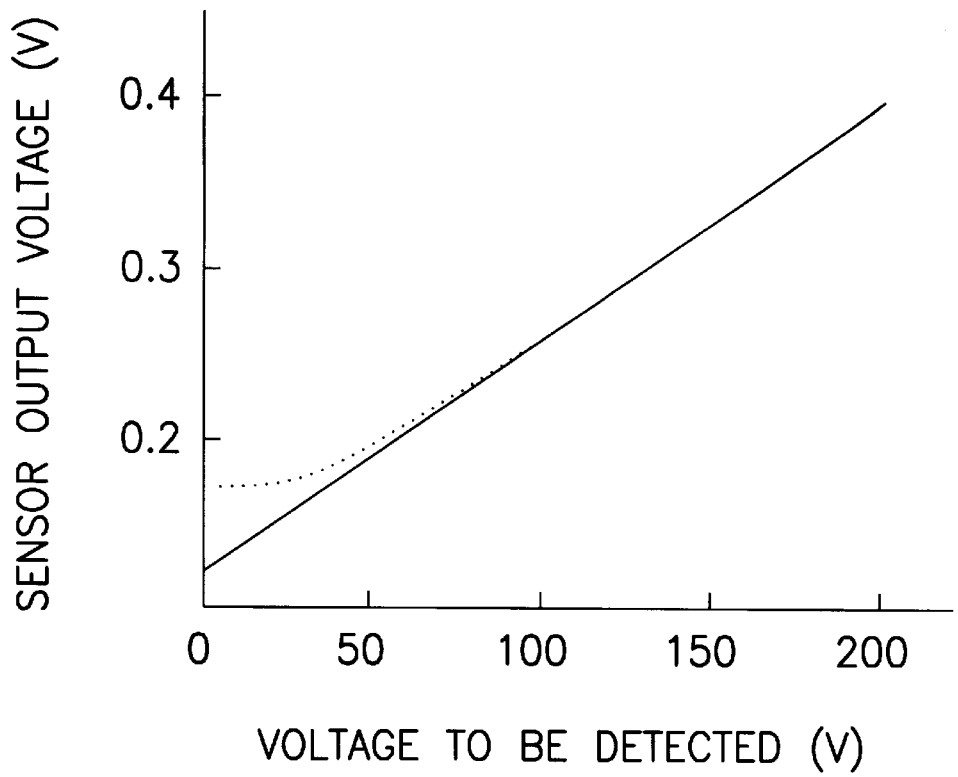
FIG. 4 is a graph showing the relationship between a voltage to be detected and a sensor output voltage.
Figure 5:
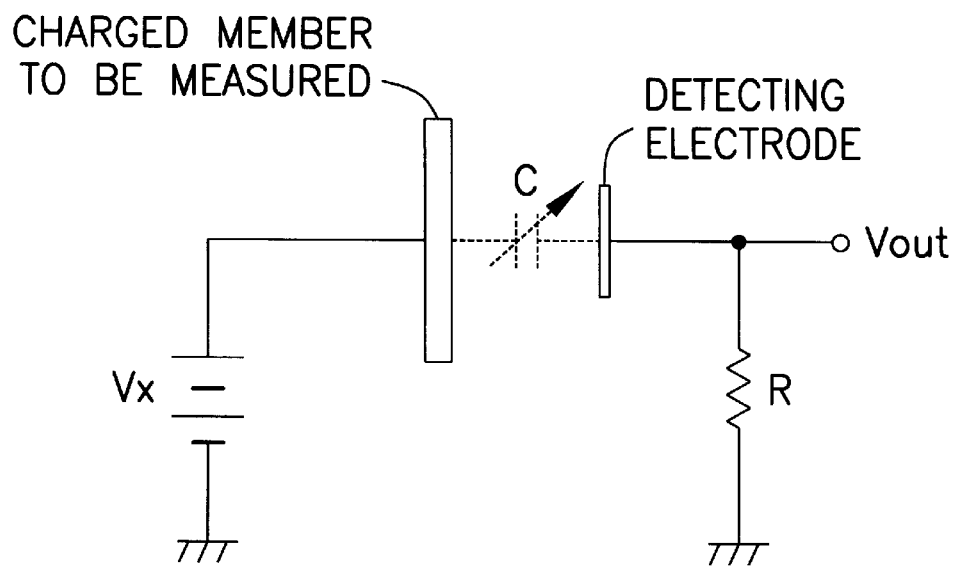
FIG. 5 is a diagram for explaining the principle of measuring a surface potential of a charged member to be measured.
Figure 6:
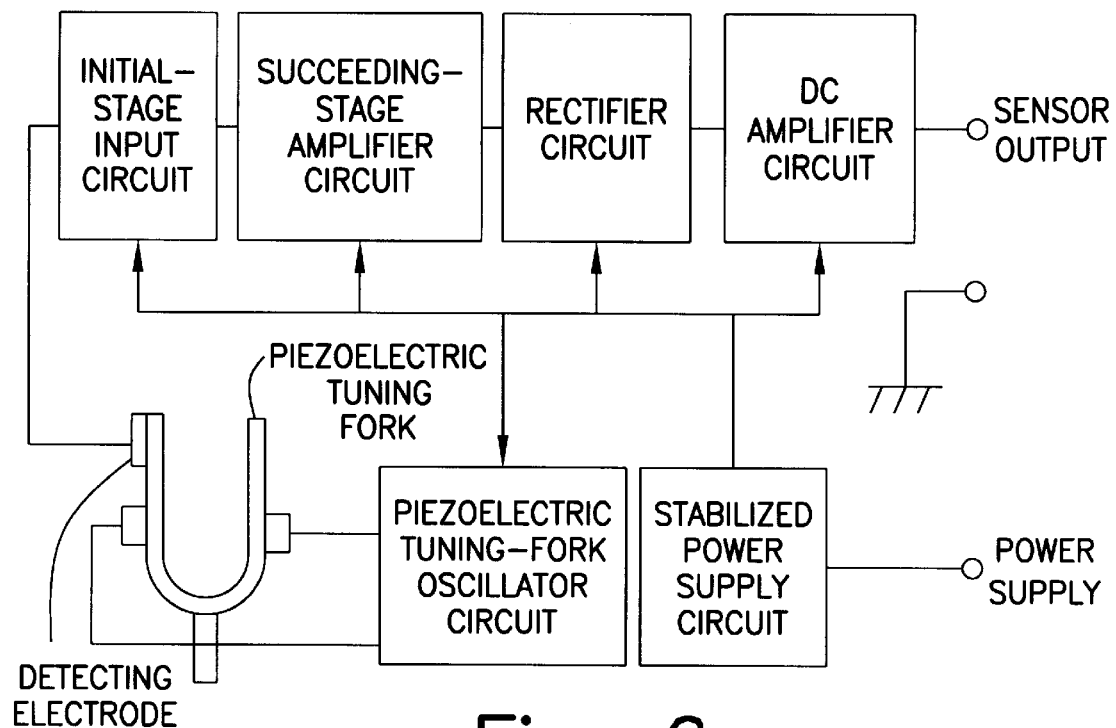
FIG. 6 is a general block diagram of a conventional surface potential sensor.

FIG. 4 is a graph showing the relationship between a voltage to be detected and a sensor output voltage obtained by the surface potential sensor having the circuit shown in FIG. 1. In the graph of FIG. 4, a solid line represents a characteristic resulting from the embodiment of the present invention, and a broken line represents a characteristic resulting from the conventional surface potential sensor shown in FIG. 7. For the conventional surface potential sensor, as mentioned above, the sensor is greatly affected by the noise superposed on the reference source voltage, and extraneous noise cannot be sufficiently shielded. This reduces an S/N ratio. In the range where the voltage to be detected is low, therefore, the noise component becomes relatively large and the apparent sensor output is increased. By contrast, in the surface potential sensor of the present invention, a sensor output substantially proportional to a true surface potential can be obtained even in the range where the voltage to be detected is low, and measurement accuracy in that range is improved.

As described hereinabove, according to the first and second aspects of the present invention, even with noise superposed on the reference source voltage, no noise component appears in a difference between the AC component output from the initial-stage input circuit and the reference source voltage. The subsequent-stage amplifier circuit can therefore perform AC-amplification without being affected by the noise component. It is thus possible to increase an S/N ratio and improve measurement accuracy with ease.

Also, according to the third aspect of the present invention, since the detecting electrode and the gate terminal of the FET or the input circuit portion leading to the gate terminal are shielded by the reference source voltage line and the ground electrode, the sensor is less affected by extraneous noise and an S/N ratio is further increased. As a result, linearity of the sensor output voltage versus the voltage to be detected by the surface potential sensor is further improved, and hence measurement accuracy is increased in the range where the voltage to be detected is low.

What is claimed is:

1. A surface potential sensor comprising:
   a detecting electrode for being positioned to face a charged member for detecting a surface potential of said charged member,
   an electrostatic capacitance formed between said charged member and said detecting electrode being changeable,
   an initial-stage input circuit connected to said detecting electrode for receiving a signal from said detecting electrode, and receiving a reference voltage as a source voltage supplied to said initial-stage input circuit, and
   a succeeding-stage amplifier circuit receiving an output of said initial-stage input circuit and amplifying a difference between an AC component in said output of said initial-stage input circuit and said reference voltage.

2. The surface potential sensor according to claim 1, wherein said initial-stage input circuit comprises an FET, a source of said FET being grounded, a resistor being connected between a drain of said FET and said reference voltage, said signal from said detecting electrode being applied between a gate of said FET and ground, and a drain potential of said FET being applied to said succeeding-stage amplifier circuit.

3. The surface potential sensor according to claim 2, wherein a line which supplies said reference voltage and a ground electrode are arranged in positions surrounding said detecting electrode and one of a gate terminal of said FET and an input circuit portion leading to said gate terminal, sufficiently closely to provide shielding of said detecting electrode and said gate terminal or said input circuit portion.

4. The surface potential sensor according to claim 1, wherein a line which supplies said reference voltage and a ground electrode are arranged in positions surrounding said detecting electrode and said initial-stage input circuit sufficiently closely to provide shielding of said detecting electrode and said initial-stage input circuit.

5. A surface potential sensor according to claim 2, wherein said succeeding-stage amplifier circuit includes an operational amplifier for amplifying said difference.

6. A surface potential sensor according to claim 1, wherein said succeeding-stage amplifier circuit includes an operational amplifier for amplifying said difference.

7. A surface potential sensor comprising:
   a detecting electrode for being positioned to face a charged member for detecting a surface potential of said charged member,
   an electrostatic capacitance formed between said charged member and said detecting electrode being changeable,
   an initial-stage input circuit connected to said detecting electrode for receiving a signal from said detecting electrode, and receiving a reference voltage as a source voltage supplied to said initial-stage input circuit, said initial-stage input circuit including a semiconductor device having a gate terminal and first and second input-output terminals, said first input-output terminal of said semiconductor device being connected to said reference voltage, said second input-output terminal of said semiconductor device being connected to ground, and said gate of said semiconductor device being connected to said detecting electrode, and
   a succeeding-stage amplifier circuit receiving an output of said initial-stage input circuit and amplifying a difference between an AC component in said output of said initial-stage input circuit and said reference voltage.

8. A surface potential sensor according to claim 7, wherein said succeeding-stage amplifier circuit includes an operational amplifier for amplifying said difference.

9. The surface potential sensor according to claim 7, wherein a line which supplies said reference voltage and a ground electrode are arranged in positions surrounding said detecting electrode and one of said gate terminal and said semiconductor device or an input circuit portion leading to said gate terminal, sufficiently closely to provide shielding of said detecting electrode and either said gate terminal or said input circuit portion.

* * * * *